(12) United States Patent
John

(10) Patent No.: US 6,195,576 B1
(45) Date of Patent: Feb. 27, 2001

(54) QUANTITATIVE MAGNETOENCEPHALOGRAM SYSTEM AND METHOD

(75) Inventor: Erwin Roy John, Mamaroneck, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/036,933

(22) Filed: Mar. 9, 1998

(51) Int. Cl.⁷ ........................................................ A61B 5/05
(52) U.S. Cl. .................... 600/409; 324/244; 324/248; 324/260; 324/246
(58) Field of Search ..................... 600/409, 407; 324/244, 248, 260, 261, 246

(56) References Cited

U.S. PATENT DOCUMENTS

| | | | |
|---|---|---|---|
| 5,083,571 | * | 1/1992 | Prichep .................................. 128/731 |
| 5,282,474 | * | 2/1994 | Valdes Sosa et al. ................ 128/670 |
| 5,293,867 | * | 3/1994 | Oommen ................................ 128/630 |
| 5,307,807 | * | 5/1994 | Valdes Sosa et al. ............. 128/653.1 |
| 5,752,514 | * | 5/1998 | Okamura et al. .................. 128/653.1 |
| 5,885,215 | * | 3/1999 | Dossel et al. ......................... 600/409 |

* cited by examiner

Primary Examiner—Marvin M. Lateef
Assistant Examiner—Eleni Mantis Mercader
(74) Attorney, Agent, or Firm—Eliot S. Gerber

(57) ABSTRACT

A magnetoencephalogram (MEG) method and system for detecting and analyzing the magnetic effects of brain waves uses a dewar having a helmet-shaped cavity and an array of magnetic field detectors arranged in an array. In one embodiment the field detectors are located in the same relative locations as electrodes in the EEG 10/20 system. A subject's MEG data is compared to a normative spontaneous and/or evoked MEG database collected using standardized detector positions and sensory stimuli and/or to a normative QEEG database simultaneously or previously constructed using corresponding standardized electrode positions and sensory stimuli. Statistical parameters in these databases assess the probability that MEG features derived from a subject are within normal limits. Deviations are indicated on interpolated statistical probability maps color-coded to indicate degree of abnormality. Multivariate statistical analyses may be used to categorize brain disorders in individual patients.

42 Claims, 2 Drawing Sheets

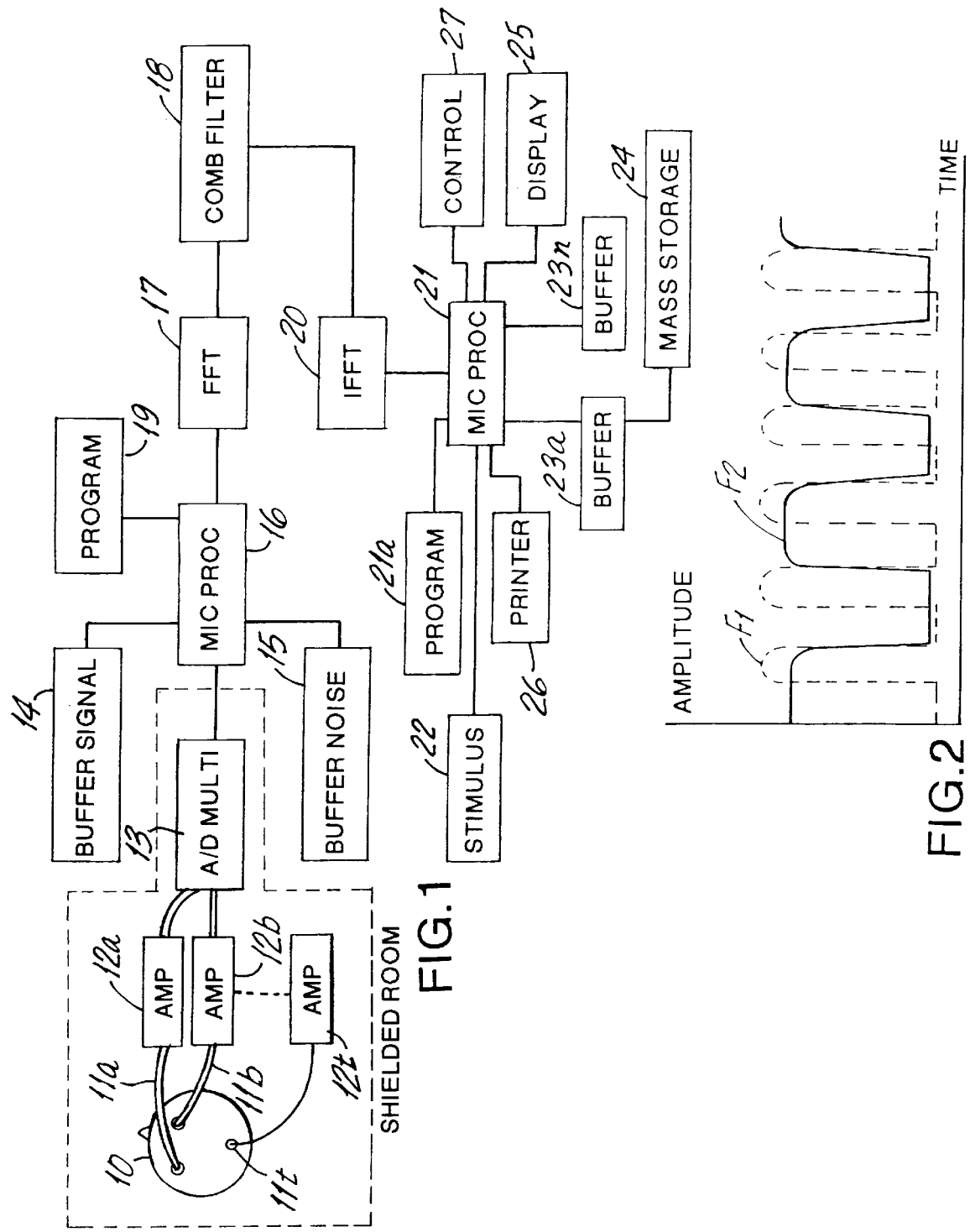

QUANTITATIVE MAGNETOENCEPHALOGRAM SYSTEM AND METHOD

FIELD OF THE INVENTION

The present invention relates to medical systems and methods and more particularly to the study and analysis of human brain waves detected by a magnetoencephalogram.

BACKGROUND OF THE INVENTION

At the present time it is known that faint electrical and magnetic waves in the human brain may be detected and analyzed by non-invasive methods. There are many patents and publications in the fields of EEG (electrocencephalogram) and MEG (magnetoencephalogram) which describe the medical benefits made possible by brain wave analysis. For example, it may be possible to detect neurological disorders such as epilepsy, and psychiatric disorders, such as unipolar depression.

The EEG is widely used in clinical practice and is commonly found in neurological clinics and hospitals. Although there has been considerable research activity and resulting publications using MEG, it is generally believed, especially by clinical neurologists, that better medical diagnoses may be obtained using EEG. However, it is usually necessary, using presently available EEG methods, to retain a subject in the EEG apparatus for a prolonged time period, over 30 minutes, to obtain a meaningful set of data. Appreciable additional time is required for electrode application and removal. However, MEG has not been widely used in a clinical setting, although it possesses certain advantages compared to EEG. These advantages include:

(i) In MEG the dewar container may be easily placed on or close to the patient's head. The pick-up detectors are within the dewar container and there may be as many as 122 or more magnetic-detectors able to detect magnetic brain wave effects at 122, or more, separate areas on the surface of the patient's scalp. In contrast, in EEG, it may be time-consuming, messy and even painful to make a satisfactory low impedance connection with the patient's scalp, especially if the patient has a large head of hair. Generally fewer electrodes are used, for example, a widely used electrode placement system is the "International 10/20 System" which provides 19 active EEG electrodes.

(ii) The time required for a testing session may be greater in the case of EEG than MEG. In EEG it is important to repeatedly test the impedance of the EEG electrode connection to the scalp. Often the patient moves and disturbs that connection, which requires that the electrode be re-connected. Such monitoring and re-connection is not required with MEG systems. In addition, it is believed that MEG is less adversely affected by tissue artifact, such as eye movement, than EEG.

(iii) The MEG has certain theoretical advantages over the EEG. In MEG the neuromagnetic field vector B provides directional information about the orientation of the source. The neuromagnetic field vector B is not distorted by passage through the brain and scalp, as are the EEG electrical brain wave signals. The MEG is an absolute measure of source strength and not measured with respect to a reference, i.e., the patient's body, as in EEG.

Despite these advantages, MEG has generally been used in universities or medical centers for research and not for clinical applications. One reason is cost, as MEG systems cost two to three million dollars. Another reason is the inability to analyze the MEG data to produce meaningful clinical results.

An MEG system may require a magnetic shielded room (high Mu room) which is large enough for the dewar part of the MEG system and the patient. The MEG system is sufficiently sensitive, if not enclosed in such a room, that the magnetic influence of even a passing car would create sufficient noise to drown out brain wave magnetic signals.

A typical MEG uses 50–130 magnetic detecting coils in a dewar (insulated vacuum container). Each of these coils is a Superconducting Quantum Interference Device (SQUID) which is operated at a cryogenic temperature. The coils may be brought as close to the subject's scalp as the thickness of the dewar, for example, 1 cm. The SQUID has one or two Josephson junctions which exhibit quantum interference effects. The MEG systems are generally large, complex and costly compared to EEG systems.

In one type of MEG system, available from Neuromag Oy, Finland, the patient sits in a chair and a dewar is lowered over the subject's head.

The dewar has a helmet-shaped cavity at its end ("dewar tail") which fits over the subject's head, and contains over 100 SQUID detectors, each of which becomes perpendicular to the subject's scalp.

Another system uses a clam-shell like arrangement in which the subject lays down with his head in a cavity in a bed-like setting and an upper shield having a head cavity is lowered over the subject. That system does not have SQUID detectors at the mid-line of the scalp. In addition, the subject is lying down and not in a good position to respond to stimuli required for evoked response testing.

U.S. Pat. No. 5,243,281, assigned to Neuromag Oy, Finland, discloses a superconducting magnetometer or gradiometer for measuring magnetic fields generated by the human brain which are detected simultaneously over the entire skull. A single dewar flask contains an array of detecting coils and SQUIDS. The SQUID gain is increased using positive feedback. Integrated elements are used, each element comprising a SQUID and a magnetometer or pick-up coil. The dewar is shown as having a cylindrical body with a head-shaped (helmet-shaped) cavity at its lower end (dewar tail).

Alternative dewars with a plurality of magnetometers or gradiometers arranged in a helmet-shaped configuration are shown in U.S. Pat. Nos. 5,339,811 and 5,713,354 to Biomagnetic Technologies. The U.S. Pat. No. 5,713,354 uses the term "biomagnetometry" to refer to the measurement of magnetic fields arising from electrical brain waves and "biomagnetometer" to refer to the device, including the SQUID detectors, which is used to measure such magnetic fields. The above-mentioned patents are incorporated by reference.

SUMMARY OF THE INVENTION

The present invention relates to improvements in the system and methods for analyzing data derived from a Magnetoencephalogram (MEG) (biomagnetometer) which is placed on the head of a human subject.

Preferably the biomagnetometer uses a dewar having a helmet-shaped cavity in its dewar tail. That cavity has a diameter of about 25 cm and is shaped to fit over the head of the subject and cover the subject's scalp.

The dewar contains an array of magnetic field detectors ("field detectors"), i.e., magnetometers or gradiometers, each of which includes a SQUID. Preferably the dewar has at least 19 field detectors whose locations correspond to the locations of the 19 electrodes of the International 10/20 EEG system or its expansion to larger arrays. Alternatively, fewer field detectors may be used, although the data derived from fewer field detectors will not be as complete as using a full set of 19 field detectors. If use is made of an available dewar having a large number (50 or more) field detectors, a case-by-case study should be conducted to select and use only those field detectors which most closely correspond in physical location or sensitivity to the physical locations or sensitivities of the 19 active EEG electrodes in the International 10/20 System.

It is important that the subject's head be aligned and held steady within the helmet-shaped cavity of the dewar tail. This alignment of the subject's head within the dewar's cavity permits a reasonably close approximation to the desired locations of the field detectors. The objective is to place the field detectors in the same relative positions, close to the subject's scalp, as if they were EEG electrodes in the 10/20 system. For example, the mid-point of the subject's head may be determined by aligning a mark placed on the subject's nose one-half of the distance between the inner edges of his eyes with a fiducial mark on the dewar tail. The subject's head may be held firmly in place using inflatable bladders (cuffs) between the head and the dewar tail.

This solves the problem of roll (rotation) about x axis); but not the problems of pitch (rotation about y axis) or yaw (rotation about z axis), where the z axis is the vertical axis through the subject's head. Yaw and roll may be prevented by maintaining the subject's head level (yaw) and without rotation (roll) in relationship to fiducial marks on the dewar tail.

The analog signals from the field detectors are amplified using conventional MEG amplifiers and converted from amplified analog signals to digital data (A/D converter). The digital MEG data is analyzed using the techniques and databases of QEEG or QEP (QER) (quantitative EEG or evoked potentials/evoked responses). It may be expected that the methods and databases of QEEG/QER would not be directly applicable to MEG for various reasons including the following: (i) the different numbers and locations of EEG electrodes compared to MEG field detectors, (ii) the different frequency bandwidths of the EEG and MEG signals, (iii) the types of stimuli to provide evoked responses (ERs) which have been used in MEG and EEG systems are different, and (iv) the different uses to which MEG and EEG have been employed i.e. source location in MEG and discrimination between abnormal brain functions and normal groups in QEEG.

Because the MEG and EEG arise from the same electrical generators in the brain, it is reasonable to assume that quantitative analysis of the MEG will reveal features closely resembling that of the EEG. In order to establish the degree of correspondence, the simplest solution is to directly map the points of the MEG frequency spectrum onto the EEG frequency spectrum by a scaling factor to adjust the power at each frequency. The MEG and the EEG closely resemble one another with a power spectrum from 0.1 to 50 Hz, Tiihonon J, Hari R, Kajola M, Karhu J, Ahlfors S, Tissari S, "Magnetoencephalographic 10 Hz rhythm from the human auditory cortex", *Neurosci. Letters* 129:303–305, 1991 (Tiihonen et al,1991). In this patent, the MEG bands have been given the names of their corresponding EEG bands, the EEG bands being Delta 1 (0.5–1.5 Hz), Delta 2 (1.5–3.5 Hz), Theta (3.5–7.5 Hz), Alpha (7.5–12.5 Hz), Beta 1 (12.5–25 Hz) and Beta 2 (25–50 Hz). An accurate mapping between the two methods may be obtained experimentally by simultaneously recording the EEG and MEG and analyzing their spectral covariance or proportionality. It is believed that such experimental data would be correct regardless of the subject i.e. that the mapping would be uniform and not subject dependent.

In order to simultaneously take QEEG and QMEG (Quantitative MEG) measurements, special EEG electrodes are required which are thin and transparent to the weak magnetic fields on the scalp. Preferably a MEG magnetic field coil is directly aligned with each electrode of the 10/20 system. In this way the QEEG and QMEG should provide the same results—one should verify the other. This use of both QEEG and QMEG is intended primarily for research and not for routine clinical or brain function screening because of the time and difficulty in securing the EEG electrodes, even if they are in an elastic cap or helmet.

It is not possible to use all of the stimulation methods used in EEG systems to obtain evoked responses, as some of them generate magnetic noise. For example, visual stimulus may not be provided by a conventional TV monitor due to magnetic noise generated by its CRT. Standardized values of ER features have been obtained using specific stimuli. Such stimuli should be as closely as possible reproduced using the MEG system, however using devices which do not generate magnetic noise.

It is believed a database of QEEG/QER may be applicable to MEG data collected under similar conditions and similar detector positions. A QEEG/QER database has been obtained using the full 10/20 system. In thousands of cases, monopolar recordings have been taken and bipolar montages constructed by computer simulations. Generally 57 electrode combinations were computed or derived, 19 monopolar, 19 coronal biopolar and 19 sagittal bipolar, recorded using standardized conditions and stimuli which yield EEG and EP data. Numerous quantitative measures of absolute power, relative power, coherence, symmetry, and of covariance matrices across selected sets of leads and measures were extracted from artifact free recordings. In QEEG, in general, the features from an individual are compared on a feature-by-feature basis, to data collected from a normal group. Using the mean, $\overline{X}$, and standard deviation, SD, of the normative distribution for each feature, x, the value of the individual subject $\overline{X}$ is transformed to a Z-score, where $Z=[X-\overline{X}]/SD$. Generally the subject's data must be adjusted by the computer by a regression equation or an experience based table, to take account of the subject's age; see U.S. Pat. No. 4,279,258, incorporated by reference. Since normative data are free of cultural or ethnic bias, there is no need to adjust for other factors such as race, education, physical condition or other non-neurological factors, but transformations to achieve Gaussianity are usually required.

A data set is acquired from a subject using a MEG system and analyzed using quantitative methods. This may permit the acquisition of a data set which is acquired more rapidly than using EEG. For example, instead of a session lasting 30 minutes to two hours, as in some EEG testing, a sufficient data set may be acquired in 5–10 minutes using an MEG system and QMEG.

This permits many more patients/subjects to be analyzed in a day. For example, presently only 4–6 patients a day can usually be analyzed in a clinical EEG system; but using the present invention it may be possible to analyze the MEG of 50–100 patients per day. The MEG system, with such faster processing of the subjects, becomes cost effective, for example as a screening system.

The basic theory of the present invention is that there exists a replicable correspondence between the amplitude and location of the absolute powers of the electrical signal and the magnetic B vector. By "replicable correspondence" is not meant that they are the same, but only that a set of scaling factors may be applied to convert one to another. This is important because years of effort, and millions of dollars of research, has been devoted to obtain an extensive database of EEG quantitative measures ("QEEG").

It is believed that, with the proper scaling factors, these data may be directly and automatically applied, in a computer system, to evaluate the power spectra of MEG data sets. It is further believed that relative power (i.e., normalization of the power spectra within each channel) may also be correlated with the QEEG database.

Whether or not such equivalence can be established, it is believed that the systematic quantitative analysis of the power spectra and cross-spectra obtained from a set of MEG sensors, the construction of standardized features such as the absolute power, relative power, coherence and symmetry in frequency bands analogous to those conventionally used in QEEG, the computation of covariance matrices across sets of sensors and measures, and the statistical evaluation of each such feature to an age-appropriate normative database, will greatly facilitate adoption of the MEG for routine clinical diagnosis and treatment selection.

BRIEF DESCRIPTION OF THE DRAWINGS

In the accompanying drawings:

FIG. 1 is a block schematic drawing of the apparatus of the present invention;

FIG. 2 is a chart showing the timing of two stimulations, for example, auditory clicks and somatosensory skin voltage pulses, which are simultaneous and out-of-phase.

DETAILED DESCRIPTION OF THE INVENTION

Figure 3:
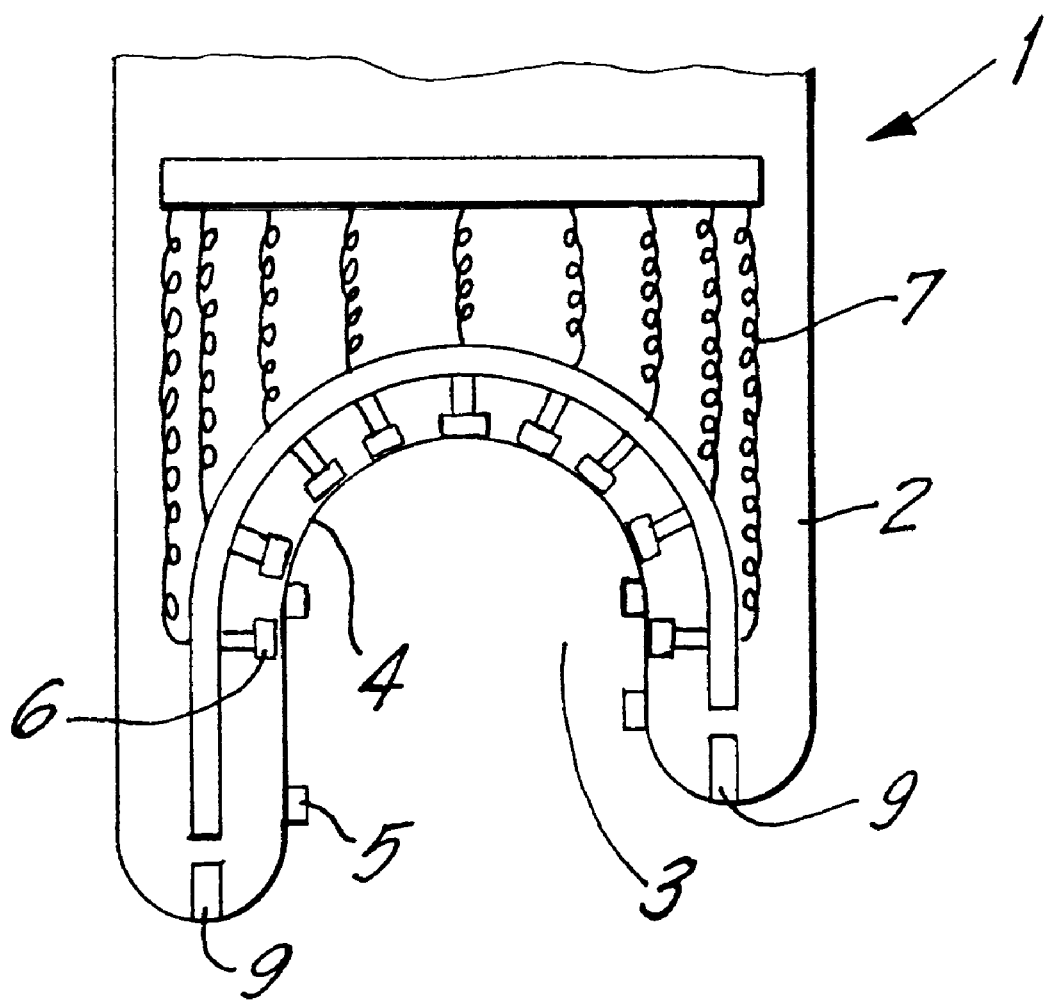
FIG. 3 is a side view, partly in cross-section, showing a MEG dewar tail on a subject's head.

I. Correspondence Between EEG Electrodes and QMEG-SQUIDS

In order to use the QEEG database it is first necessary to establish a correspondence between the EEG electrodes used to establish that database and the location of the magnetic field detectors in a MEG system.

In theory, the EEG and MEG signals are generated at the same node (source) simultaneously. The EEG signal suffers from blur distortion as that micro-volt signal travels through the brain, cerebral spinal fluid, low-conductivity skull and scalp to the recording EEG electrodes. However, both the EEG and MEG signals travel the same path (same direction at same speed). Consequently, despite the blur distortion, there should be a high correlation between the amplitude and relative frequency of the EEG and MEG signals at each area (site) on the scalp.

The first problem is to associate each EEG electrode in the 10/20 system with one or more SQUIDs in a 50–150 SQUID array. This, in effect, initially throws away the spacial resolution that is obtainable in a large SQUID array.

The simplest method is to associate each EEG electrode with only one SQUID. The data from the other SQUIDs is not used. Alternatively, one may take into account data from the 3–6 MEG detectors which are closest in location to the locations of the corresponding EEG electrodes.

II. The MEG System

As shown in FIG. 3 the MEG system includes a dewar 1 having a dewar tail 2 with a helmet-shaped cavity 3 and fiducial marks 9. The wall 4 facing the subject's head 10 (FIG. 1) has inflatable thin bladders (cuffs) 5 positioned between the sensors (MEG field detectors). The sensors 6 are mounted in an array on support shell 2 (its supports are not shown). The sensors 6 are connected by wires 7 to a printed circuit board (motherboard). Each sensor 6 comprises a detector coil (flux transformer) and a SQUID. All of the components within the dewar are covered by liquid helium at a cryogenic temperature.

As shown in FIG. 1 nineteen MEG detectors $11a$–$11t$ are connected to nineteen amplifiers $12a$–$12t$ which, in turn, are connected to an analog-to-digital multiplexer 13 (A/D multiplexer). The multiplexer 13 samples the amplified analog brain waves at a rate compatible with the bandwidth of the amplifiers or is programmed to provide spontaneous or evoked MEG outputs sampled at the appropriate different rates. The multiplexer 13 provides, at its output, sets of digital data, representing spontaneous (ongoing brain wave) and MER (Magnetic Evoked Response) analog signals. The multiplexer 13 is connected to "buffer signal" 14, which stores the signal, and "buffer noise" 15, which stores samples of the "noise", that is, amplifier output of MEG when no stimuli are delivered to elicit MERs. The buffers 14, 15 and A/D multiplexer 13 are connected to the dedicated computer microprocessor 16. For example, the microprocessor may be an Intel "Pentium" (TM) or a digital signal processor, such as the TM5320C32. The microprocessor 16 is connected, through its dedicated 512-point FFT 17 (Fast Fourier Transform) to digital comb filter 18 and is controlled by software program 19.

The comb filter is connected to, and controls, the IFFT 20 (Inverse Fast Fourier Transform). The output of the IFFT 20 is connected to the system microprocessor 21, for example, Intel "Pentium" (TM). The microprocessor 21 is connected to, and controls, the magnetically silent stimulus devices 22 (lights, loudspeaker, shock device, etc.), the system digital storage buffers $23a$–$23n$ (only two being shown), the mass storage 24, such as a hard disk, the display 25, such as a CRT, a print-out printer 26 and keyboard control panel 27. The microprocessor 21 operates under control of software program $21a$.

The digital comb filter 18 may be as described in U.S. Pat. No. 4,705,049, incorporated by reference herein. The comb filter may be considered a series of band pass and band stop filters which are responsive over a selected range. The selected range is expected to be below 3000 Hz. The band pass filters will be selected on the basis of experimentation to improve the signal-to-noise ratio. Such experiments may usefully use the F ratio of variance at each frequency. The band pass filters are the "teeth" of the comb which are selected so as to accord with the frequencies in which the signal-to-noise ratio is acceptable. The band-stop filters are selected to be at frequencies in which the noise is excessive. MEG systems are very sensitive to outside magnetic fields and it is believed that the use of a comb filter will decrease the adverse effects of such noise, providing reliable, rapid detection of the MER.

The multiplexer 13 is programmed to obtain samples of the signal and of the noise. The "noise" is preferably obtained when there is an absence of evoking stimuli and the "signal" is obtained during stimulation, beginning with presentation of the stimuli or after a pre-selected delay.

The program 19 with its controlled microprocessor 16 condition the input signals and insure that they are valid biological signals. Such validation checks on the input signals include periodic calibration measurement and continuous automatic artifact rejection algorithms.

III. Testing of the Subject

The microprocessor 21 automatically provides a timed set of stimuli from stimulator 22 which may be an audio sound from a speaker or earphones to provide Auditory Magnetic Evoked Response (AUMER), a visual signal from a light flash to provide Magnetic Visual Evoked Response (VMER) or a tactile signal from a vibrator to provide Somatosensory Magnetic Evoked Response (SMER). Visual flashes may be delivered using fiber optic cable connected to goggles and flashing randomly or periodically. Auditory clicks, about 100 db, may be delivered through a stethoscope earpiece by air conduction tubes from a speaker outside the shielded room. The rate of stimulus is preferably 7–50/second and most preferably 34–45/second, i.e., eliciting a 40 Hz auditory steady-state magnetic evoked response (40 Hz). Regular audio clicks and rare visual flashes or tactile stimuli may be combined into a randomly mixed stimulus sequence, with the AUMER elicited by the rare stimulus providing the cognitive "Event-Related Magnetic Response" (ERMR) corresponding to P300 (P3) in the AER. The patient's brain will respond to these stimuli, providing Evoked Magnetic Responses (EMRs) which are averaged to reduce noise, providing an "Average Magnetic Evoked Response" (AMER). Sample size varies with stimulus mobility, ranging from about 100 (VMER) to about 512–2048 for Brain Stem Auditory Magnetic Evoked Response/Brain Stem Somatosensory Magnetic Evoked Response (BSAUMER/BSMER).

The AMER is the sum of samples time-locked to the onset of the stimuli divided by the number of samples, to provide an updated average.

The MEG system automatically and continually collects ongoing brain waves and also challenges the subject with regularly repeated periods of stimuli to provide evoked responses.

The MEG system provides a timed sequence of concurrent stimulations, in one or two sensory modalities (modes), to the subject. Preferably, stimulations are used in two different modalities, such as an audio tone or click at one repetition rate (F1) and electrical shocks to peripheral nerves at a second repetition rate (F2). The stimuli, although concurrent, are at different prime number frequencies to permit separation of different ERs and avoid interference. Such concurrent stimulations permit a more rapid, and less costly, examination and provide the subject's evoked responses more quickly.

The MEG system collects a set of artifact-free MEG (on-going brain waves) and AUMER and SMER samples in the examination session. The data acquisition is automatic and the computer removes or excludes artifacts, by thresholding regression or other techniques, such as using Delta 1 to detect eye movement artifacts and Beta 2 to detect EMG artifacts (see definitions below).

IV. Analysis of Data

1. Spontaneous Rhythms

Preferably a session contains 60 seconds of artifact-free MEG of on-going brain waves as well as one or more AERs averaged using 100–2048 stimuli. The MEG system then subjects the data to spectral analysis using very narrow band (about 0.5 Hz steps) FFT (Fast Fourier Transform) and ER factor analysis or peak detection. Mean values and standard deviations calculated across 24 2.5 sec epochs are obtained for absolute $(uv)^2$ and relative (%) power in the Delta 1 (0.5–1.5 Hz), Delta 2 (1.5–3.5 Hz), Theta (3.5–7.5 Hz), Alpha (7.5–12.5 Hz), Beta 1 (12.5–25 Hz) and Beta 2 (25–50 Hz) wide frequency bands (or similar wide bands found to covary with the above-defined EEG bands). Additional measures may be obtained defining other wide bands or by computing sensitive indices such as $$\frac{\text{delta plus theta}}{\text{alpha plus beta}} \text{ or } \frac{\text{theta}}{\text{alpha}}$$

and calculating the ratio of such combined variables or of univariate measures of successive samples of MEG/MER relative to baseline values.

Statistically significant thresholds can be defined for each of these alternatives (Section V). Numerous multivariate measures are obtained by computing the covariance matrix for selected bands across selected combinations of detectors for every such epoch and the average covariance matrix is calculated. The Mahalanobis distance can be used to quantify such composite measures relative to normative matrices. Coherence and voltage gradients are also determined between each detector and every other detector separately for each band and for the total signal.

2. Magnetic Evoked Responses

The "latency" is the time period following presentation of a stimulus until a particular response component occurs. The interval between successive ER (Evoked Response) components is especially reliable as an indicator of brainstem state.

The electrical brain stem auditory evoked response (BAER) has, in normal subjects, 5 peaks. These latencies are expressed as milliseconds from the stimuli and are closely similar in shape and latency across neurologically normal persons. The first 5 positive peaks, in response to click (auditory) stimulus, are auditory nerve, cochlear nucleus, superior olivary complex, lateral lemniscus and inferior colliculus. The Peak I–Peak V latency interval is probably the preferred BSAUMER indicator to use. For example, the interval between Peak I of the Electrical Brainstem Auditory Evoked Response (BAER), arising from the arrival at the brainstem of an incoming stimulus via the auditory nerve, and Peak V, arising from arrival of that information at the inferior colliculus nucleus in the diencephalon, in normal persons older than 1 year, is approximately 4.0±0.2 milliseconds, which represents the time required for normal transmission through the brainstem.

Another useful indication of the subject's state is the brainstem somatosensory magnetic evoked response (BSMER). It is believed that the successive peak latencies reflect, in order, the activation of the dorsal column nuclei, medical lemniscus, thalamus, sensory radiation and the first cortical synapses (P25 and P45). The PI–PV latency interval for the BAUMER, and the doral column nucleus (PA) to somatosensory cortex (PV) latency interval for the BSMER (central conduction time—"CCT") are measured.

If auditory stimuli are presented at rate F1 Hz and somatosensory at rate F2 Hz, the power in FFT at F1 and F2 is computed and used to provide a quantitative indicator of the arrival of auditory stimuli (F1) or somatosensory stimuli (F2) at the cortex (section V).

The mid-latency (MLAER) responses at about 25 and 50 ms represent the response of the auditory cortex to incoming information and should be assessed with the 40 Hz SSER. If the auditory stimulus is 40 clicks/sec. and an average ER is computed using an analysis epoch of 100 ms, the steady state evoked response (SSMER) will reflect the arrival of auditory information to the cortex. The normalized sum of the square root of the first derivative calculated at 0.5 MS intervals across the 100 MS window of the SSMER, is called the auditory magnetic response index (AMRI). The AMRI is a desirable element in the set of ER features.

The feature extraction method for cortical evoked responses involves alternative ways to describe ER signal strength, variability and interhemispheric symmetry. These features are extracted for latency domains: 80–140, 140–200 and 200–500 msec. Measures of signal strength ("features") include absolute peak-to-peak (p-p) amplitude and "normalized" p-p amplitude. Normalized p-p amplitude is obtained by defining the largest amplitude as 100%, and other measurements are scaled relative to that maximum. Measures of ER variability include the standard deviation of the p-p amplitude(s), the variance ($s^2$), and log variance (log $s^2$). The standard deviation of the p-p amplitude (s) is an rms measure: rms=$(^sPmax)^2-(^sPmin)^2$, where s is the standard deviation, and $P_{max}$ and $P_{min}$ are the largest positive and largest negative peaks, respectively within a particular latency domain (100–250 msec or 250–500 msec). Log $s^2$ is computed because s itself is not normally distributed. A measure of signal-to-noise ratio (S/N) is computed as well, where "signal" is the p-p amplitude, and "noise" is its standard deviation. The principal measure of bilateral ER symmetry is the Pearson product-moment correlation (r) across the time bins, computed for ERs recorded, when using six or more sensors, from homologous derivations over left and right hemispheres corresponding to 10/20 electrode positions ($C_3$ vs. $C_4$, $F_3$ vs. $F_4$, and $P_3$ vs. $P_4$, etc.), and referred to as "interhemispheric coherence". The square of the product-moment correlation coefficient ($r^2$) is also obtained for each homologous pair of sensors. Across a set of 19 or more detectors, there are thus available a large set of quantitative MEG descriptors, including cortical ER descriptors, brainstem ER descriptors, and features extracted from the spontaneous MEG.

V. Statistical Probability QMEG-MER Data Evaluation Relative to Self-Norms and Normative Databases Every feature extracted from an individual subject is statistically compared with a normative reference database of corresponding measures obtained from a group of normal subjects of the same age. All measures must be subjected to those transformations required to achieve Gaussianity of their normative distributions.

After such transform for Gaussianity, every measure may be Z-transformed to rescale it, using the corresponding mean and standard deviation obtained from the normative reference distribution. Each Z-score is calculated in the following manner: the normal group mean, $\overline{X}$, for a particular measure is subtracted from the value X for that measure obtained from the X–$\overline{X}$ subject. The difference X–$\overline{X}$ is divided by the standard deviation, SD, of that measure. Thus, $$Z = \frac{(X - \overline{X})}{SD}.$$

If the distribution of a variable is Gaussian, the Z-score provides an estimate of the probability that an observed measure is "abnormal", i.e., improbable. The anatomical distribution of Z-scores for each QEEG variable may be displayed on an interpolated topographic map. A "heat" scale may be used to encode excesses in hues of red and deficits in hues of blue.

As MEG power at a given frequency equals the variance at that frequency, the ratios of power responsive to the presence versus absence of stimuli at rate F1 in a first modality (i.e., auditory stimulation F1 on/ F1 off) and at rate F2 in a second modality, (i.e., somatosensory stimulation F2 on /F2 off) are calculated. F1 and F2 are simultaneous but out of phase as shown in FIG. 2. Alternatively, auditory stimuli at F1 and tactile stimuli at F2 are continuous, evoking steady state brain responses. 10-second samples of MEG (on-going brain wave activity) are collected, FFT computed at 0.1 Hz or other small increments and an average of N samples of the FFT computed. The power in the F1 and F2 windows (Fstim) and the average power (Fav) in the adjacent windows, (for example, 40 bins (B) above and below each of the stimulation frequencies) is used to compute the value of Fs, $$B = \frac{\text{Power Fstim}}{\text{Power Fav}}.$$

These ratios, treated as as F-values, estimate the statistical probability that the auditory stimuli are traversing the brainstem and the somatosensory stimuli are traversing the spinal cord and brainstem to reach the cerebral cortex. In addition, using trigger pulses at the F1 and F2 frequencies, the microprocessor may compute the actual waveshapes of averaged brainstem auditory magnetic evoked responses (BAUMER), 40 Hz SSMER, and brainstem somatosensory magnetic evoked responses (SMER).

VI. Statistical Probability QMER

Another useful method in the analysis of MER features is "factor analysis", which has been applied to electrical AERs, see John U.S. Pat. No. 4,913,160, incorporated by reference. The subject is challenged by a programmed sequence of stimuli. The subject's MEG responses to those stimuli are averaged to generate averaged magnetic evoked responses (AMERs).

The computer will then attempt to reproduce (reconstitute) each waveshape of the AMER by matching it to a database of waveform factors (basis waveshapes) in the computer's memory. The shape of the wave form factors are arbitrary waveforms constructed on the basis of experience or a "varimax procedure", see U.S. Pat. No. 4,913,160 at column 5, lines 43–66. The matching procedure is to first find the closest basis waveshape ("1st Factor") to a particular AMER and subtract it, leaving an unmatched residual waveform ("First Residuals"). Secondly, the unmatched residual waveform is matched with the set of basis waveforms to find the closest match. That matched basis waveform ("2nd Factor") is subtracted, leaving a smaller residual waveform ("Second Residuals"). This matching and subtraction procedure is repeated, generally 4–8 times, until a selected residual of power is reached ("Final Residuals") which is not further matched. This residual variance estimates that portion of the AMER total variance which lies outside the "normal signal space."

Each AMER waveshape from each MEG detector is compared to pre-formulated waveform factors stored in computer memory to determine the weighting that each pre-formulated waveform factor contributes to each AMER, to thereby produce a factor score. The computer system then subjects this factor score to Z-transformation. Each of the factor scores is compared to the distribution of such scores in norms stored in computer memory to calculate Z-scores for each factor, to produce a determination of normality or the degree of abnormality of each ER waveshape.

The normality or degree of abnormality of the waveshape in each brain region of the waveshape in the latency domain of every factor (component) may be displayed on a series of interpolated or sectored topographic maps, each of which is a head diagram on which each area of the head represents a MEG detector location, color-coded for the statistical significance of local deviations from an expected waveshape at the corresponding latency.

The waveshapes produced by "normal" persons (normal brain functioning) can be accurately reconstructed by a set of factors with weightings (factor scores) within the normative range. Waveshapes produced by "abnormal" persons cannot be adequately reconstructed, revealing significant Z-values for the required factor scores and/or significant residual variance. Further, the waves of "abnormal" subjects may be matched to different categories of "abnormal". For example, a subject with unipolar depression will generate sets of abnormal factor scores, in response to standardized stimuli, which are similar to those from other subjects with unipolar depression and dissimilar to normal subjects or to subjects with bipolar depression.

The concept of factor analysis may be described in the following formula:

Wi is a set of AMER waveshapes (magnetic evoked responses) which are (i) responses at different head areas (different MEG detectors) to the same stimulus, or (ii) responses to different stimuli at the same scalp detector.

$a_{ii}$ is the contribution (factor score) of the factor F1 (first basis waveshape) and $a_{12}$ is the factor score of the factor F2, etc. Then:

$$W_1 = a_{11}F_1 + a_{12}F_2 + a_{13}F_3 \cdots a_{1k}F_k \quad \text{(Eq. 1)}$$

$$W_2 = a_{21}F_1 + a_{22}F_2 + a_{23}F_3 \cdots 2_{2k}F_k$$

.
.
.

$$W_N = a_N F_1 + a_{N2}F_2 + a_{N3}F_3 \cdots a_{Nk}F_k$$

K is the number of factors that will describe a satisfactory amount of the energy in a set of N AMER waveforms. Generally K is 7 or less and is considerably less than N, the number of AMER waveforms in the set.

The computer memory contains a set of "General Factor Waveshapes", $F_j(t)$, capable of reconstructing the individual waveshapes $W_i(t)$ recorded from any MEG detector position i in any normal subject as a weighted sum. This set can be defined by submitting a normative set of AMER waveshapes collected from an array of MEG detectors to principal component analysis in time domain, followed by Varimax rotation. Thus, $$W_i(t) = \sum_{j=1}^{k} a_{ij}F_j(t) \quad \text{(Eq. 2)}$$

For each MEG detector position i, the mean value $a_{ij}$ and standard deviation or $\sigma_{ij}$ describes the distribution of contributions of factor j to Wi in the normal population. A set of waveshapes $W_i(t)$ recorded from a subject will utilize these normative data to quantify abnormal AMER morphology, by computing the Z-transform of the factor score, $a_{ij}$, to obtain the factor Z-score, $Z_{ij}$, as follows:

$$Z_i = \frac{a_{ij} - \overline{a_{ij}}}{\sigma_{ij}} \quad \text{(Eq. 3)}$$

wherein:
$a_{ij}$=factor score defining the contribution of factor j to waveshape recorded from detector position i in subject
$\overline{a_{ij}}$=mean value of $a_{ij}$ in normal population
$\sigma_{ij}$=standard deviation of distribution of $a_{ij}$ in normal population $Z_{ij}$=factor score resealing the deviation of $a_{ij}$ from $\overline{a_{ij}}$ into units which reflect the probability of abnormality The Z-transform provides the common metric of "relative probability" dimensions (units) in which all features are stated (the probability of obtaining the observed value by chance in a member of the normal group). The Z computation characterizes each individual's index value as a number of error steps from the mean control value and indicates the relative probability that this value might occur by chance.

Using factor Z-scores to replace the original weightings (factor scores), Equation 2 can be rewritten as:

$$W_i(t) = \sum_{j=1}^{k} Z_{ij}F_j(t) \quad \text{(Eq. 4)}$$

The factor waveshapes $F_{ij}$ and $\sigma_{ij}$ are ascertained for any defined stimulus condition and the probability that the set of AMER waveshapes recorded from any subject under that stimulus condition displays abnormal morphology is assessed.

Thus, the full set of AMER's of the subject can be reconstructed as linear combinations of the general Factors $F_j(t)$, with the contribution of each factor j to every waveshape i defined by the corresponding actor score, $a_{ij}$. The factor scores $a_{ij}$ are Z-transformed under program control. This procedure decomposes the subject's AMER waveshapes to a standardized description which permits the subject's AMER morphology to be compared quantitatively to the morphologies encountered in the normal population. For cortical evoked potentials, there are a wide variety of normal waveshapes. The least square best fit reconstruction of the subject's AMER is obtained and the "reconstruction error" of each waveshape $W_i(t)$ is computed. This difference between the actual AMER and the factorial reconstruction quantifies the amount of energy in the patient's response which may lie outside the "normal signal space", and will be referred to as the residual, R, which is also Z-transformed.

The results are displayed, or example on hard copy as a data print-out or a color coded topological map of the subject's head, using the "heat" scale of colors. Scalp areas at which the subject's Z-score is highly positive will be colored bright red, while regions where Z-scores are highly negative will be colored bright blue.

VII. Discriminant Functions

The preferred method and system to compare the features extracted from the spontaneous (MEG) or evoked (MER) magnetic brain activity of the patient with a clinical reference database is to use "discriminant functions" based upon distance measures in a signal space. As mentioned above, the Z-scores are obtained for each feature,or the covariance matrix is computed across all features and all detectors, and multivariate distances of the subject from the centroid of a set of measures taken from groups of patients considered to be representative of a clinical condition of relevance are computed and are then used to estimate the probability that the patient is a member of that clinical reference group, i.e., suffers from that condition.

A further use of the MEG system of the present invention is to distinguish between patients with medical conditions which present similar symptoms, but who require different treatments. For example, an elderly male subject may present symptoms of some loss of physical coordination, lack of motivation, and some loss of short term memory. Those symptoms may indicate (i) the late onset of mental depression, which may be treatable with psychological therapy or drugs, or (ii) a vascular condition resulting in signs of dementia (transient ischemic attacks or microinfarcts) which may be treated by aspirin or anticoagulant or reduction of blood pressure, or (iii) an early stage of Alzheimer's disease or Pick's disease, which may be helped by certain newly announced drugs. If the diagnosis is incorrect, treatment may not be initiated, may be ineffective or the patient may be unnecessarily disturbed by being labeled with an ominous condition. It is believed that the MEG system may rapidly, and cost effectively, discriminate between the states (i)–(iii) on the basis of discriminant functions.

These conditions, or similar condition categories, of a subject, may be distinguished through discriminant analysis using discriminant functions. The discriminant functions may be used at two levels in a screening and/or diagnosis process. First, it may distinguish whether a subject is probably "normal" or "abnormal" as to general or specific brain functions. Secondly, if the subject is indicated as probably being abnormal, it may distinguish between alternative categories of abnormality, or of probable responsiveness to different treatments.

For example, in a screening process one might first distinguish learning disabled children ("abnormal") from non-learning disabled children ("normal"). Secondly, one might distinguish among categories of learning disabled children who have normal intelligence, namely between such children having: (i) ADD (Attention Deficit Disorder), (ii) ADHD (Attention Deficit-Hyperactivity Disorder), or (iii) SLD (Specific Learning Disorder). In addition, one may distinguish ADHD children who might respond well to the drug methylphenidate (Ritalin) and badly to methamphetamine (Dexedrine) from those who might respond well to Dexedrine and badly to Ritalin.

Discriminant functions are composed of weighted combinations of subsets of variables, the subsets being age-related Z scores. Each of the variables (each Z score) is selected, on the basis of experience and statistical analysis of groups of patients with various conditions, because it significantly contributes to the discrimination (i.e., discrimination between the conditions sought to be diagnosed). The weighting of the subsets (how much should each variable's Z score contribute toward the total discriminant score) is also based on experience, experimentation and statistical analysis, see U.S. Pat. No. 5,083,571, incorporated by reference.

The distributions of features of two groups of subjects (where the groups belong to different diagnostic categories) can be thought of as two clouds of points in a multidimensional space in which each dimension corresponds to a feature. In this case, each feature is a Z score and the diagnostic categories, in the example above, are late onset depression, vascular caused early dementia, and early Alzheimer's. The diagnostic categories are treated in pairs of groups, i.e., A, B, C categories are tested: A v. B, A v. C, and B v. C. There may be no significant differences between two groups in some dimensions (i.e., in some features) but there may be significant differences in other dimensions. A problem arises when these clouds of points overlap (i.e., when there is some degree of overlap between the two (or more) groups with respect to some features). One attempts to define a boundary through the clouds of points to create a first zone which includes as much as practicable of the first group, and as little as possible of the second group, and a second zone which includes as much as practicable of the second group and as little as possible of the first group. A third zone is defined to encompass an overlap region where no reliable classification can be made ("guard band"). In principle, a discriminant function weights the values of selected features for a new subject and adds his weighted values to specify a single point in the relevant multidimensional space. This single point then would be in one of the three zones, and the subject would be classified accordingly.

A probabilistic classification of the state of a subject can be determined using discriminant functions derived from stepwise discriminant analysis using data from groups of subjects. Each discrimination is based on n functions where n is equal to the number of states in that discrimination. The functions are defined as the sum of selected Neurometric variables, each multiplied by a coefficient. The selection of the variables and the weightings of the coefficients are matters of experience and experimentation. Generally, each variable is a Z score. The result of each function is a single discriminant score $s_i$. A classification probability, $P_i$, that a patient's state belongs to group i; where i is for example fully, partially or not in dementia, is calculated according to the following formula:

$$P_i = \frac{\exp(s_i)}{\sum_{i=1}^{n} \exp(s_i)}$$

The group (state) for which a subject has the highest probability $P_i$ is selected as a potential classification group (state).

This probability $P_i$ is then compared to a guardband cutoff level for this group $a_i$, $a'_i$, $a''_i$, where $a_i < a'_i < a''_i$, ... which correspond to classification errors $\epsilon_i$, $\epsilon_i'$ and $\epsilon_i''$, where $\epsilon_i < \epsilon i'$, $<\epsilon_i''$. For example, $\epsilon_i = 5\%$, $\epsilon_i' = 2.5\%$ and $\epsilon_i'' = 1\%$.

If $P < a_i$ then the subject is not classified. If $a_i \leq P_i \leq a'_i$ then the subject is classified in group i, with confidences $1-\epsilon_i$. If $a'_i \leq P_i < a''_i$ then the subject is classified in group i, with confidence $1-\epsilon_i'$. If $a''_i \leq P_i$ then the individual is classified in group i, with confidence $1-\epsilon_i''$. In addition to such classification, a computer print-out listing the subject's "abnormal" and "normal" features may be generated along with guidelines as to the clinical implications of abnormal features.

What is claimed is:

1. The method of detecting and analyzing magnetic fields on the scalp of the subject arising from the subject's brain electromagnetic activity, by:

(a) detecting and amplifying the magnetic fields using a plurality of magnetic field detectors positioned adjacent selected areas of the subject's scalp to produce amplified signals in a plurality of channels;

(b) converting the amplified signals into digital MEG (Magnetoencephalogram) data;

(c) automatically comparing, in a computer, the digital MEG (Magnetoencephalogram) data with a normative QEEG (Quantitative Electroencephalogram) reference database of features simultaneously or previously collected from normal subjects, the comparison being on the basis of the same features obtained at the same location of the field detectors, or a computed multiple regression equation, canonical correlation, or covariance of multiple MEG detectors for the subject, as the EEG electrodes positioned on the normal subjects which generated the QEEG database, to obtain a set of QMEG (Quantitative Magnetoencephalogram) variables.

2. A method as in claim 1 wherein the detecting of the analog magnetic fields is accomplished by positioning a helmet-shaped dewar tail over the scalp of the subject, aligning the subject's head with fiducial marks on the dewar tail, and holding the subject's head firmly in the dewar tail to prevent head movement.

3. A method as in claim 1 and selecting the areas on the subject's scalp corresponding in location to areas which at least some of EEG electrodes of the 10/20 EEG system are normally connected.

4. A method as in claim 3 wherein the digital data is derived from 19 magnetic field detectors and is compared to data derived from 19 EEG electrodes corresponding in location to the full 10/20 system.

5. A method of detecting and analyzing magnetic fields on the scalp of a subject arising from the subject's brain waves, by:
   (a) positioning or selecting a plurality of magnetic field detectors arranged in an array in a dewar tail;
   (b) bringing the dewar tail into close proximity to the subject's scalp and holding the subject's head at the dewar tail to prevent head movement;
   (c) using the magnetic field detectors to detect scalp magnetic fields and to generate analog signals therefrom;
   (d) amplifying and digitizing the analog signals to produce a set of digital MEG (Magnetoencephalogram) data corresponding to the analog signals from each magnetic field detector;
   (e) automatically, in a computer, statistically comparing features extracted from each set of digital MEG data taken under selected conditions or stimuli with mean values and SD's (Standard Deviations) in a normative MEG database, on a feature-by-feature basis, based upon QMEG (Quantitative Magnetoencephalogram) data from a normal group simultaneously or previously gathered under the same conditions or stimuli and with the brain activity MEG detectors of the normal group at the same locations as those of the subject, to obtain and assess QMEG values;
   (f) simultaneously with (b), using a plurality of EEG electrodes on the scalp of the subject to derive EEG signals;
   (g) amplifying and digitizing the EEG signals to produce sets of QEEG (Quantitative Electroencephalogram) data; and
   (h) automatically in the computer comparing each set of QEEG data with digital QEEG data from a normal group taken, simultaneously or previously, under the same conditions or stimuli.

6. A method as in claim 5 and also comparing quantitative features extracted from each set of digital MEG data with mean values and standard deviations of features extracted from digital data of a normal group which is derived from EEG signals.

7. A method as in claim 5 and positioning a plurality of the EEG electrodes both in the 10/20 position and aligned with the magnetic field detectors.

8. A method as in claim 5 and using thin and magnetically transparent EEG electrodes for the plurality of EEG electrodes.

9. A method as in claim 5 wherein the subject's digital data is derived from 19 magnetic field detectors and quantitative features derived therefrom are compared to similar features derived from data from 19 EEG electrodes corresponding in location to the full 10/20 system.

10. A method of detecting and analyzing magnetic fields on the scalp of a subject generated by the subject's spontaneous or stimulus evoked brain activity, by:
    (a) positioning an array of a plurality of magnetic field detectors closely adjacent to the subject's scalp to detect and amplify the magnetic fields from selected areas of the scalp;
    (b) converting the detected magnetic field into sets of digital data, with each set being generated by a magnetic field detector;
    (c) automatically comparing, in a computer, the sets of digital data with a normative reference database of QEEG (Quantitative Electroencephalogram) features simultaneously or previously collected from normal subjects, the comparisons being on a feature-by-feature basis, and the normal subjects having generated the database using brain wave EEG detectors at the same relative locations on their scalps as the relative locations of the magnetic field detectors on the scalp of the subject, to compute a measure of the probability that the observed value is beyond normal limits (Z- or F-score);
    (d) deriving a discriminant score based on the comparisons of (c) by selecting, weighting and combining a number of said feature-by-feature comparisons;
    (e) combining the discriminant scores to derive probabilities that the subject is classed in a specific diagnostic category;
    (f) applying selected guardbands (rule-out levels) to the probabilities to classify the subject on the basis of the probabilities; and
    (g) displaying the classification of the subject.

11. The methods of claim 1, 5 or 10 in which the normative reference databases of features are in the form of age-corrected scores which are in the appropriate dimensional units and all features from each subject and in the databases have been transformed to achieve Gaussianity.

12. A method as in claim 10 and selecting the areas on the subject's scalp which correspond in location to areas to which at least some of the electrodes of the 10/20 EEG system are normally connected.

13. A method as in claims 1, 5 or 10 and employing a SQUID as part of each magnetic field detector.

14. A method as in claims 1, 5 or 10 and employing a magnetometer or gradiometer as part of each magnetic field detector.

15. A method as in claims 1, 5 or 10 wherein the digital data derived from each magnetic field detector is log or otherwise transformed for Gaussianity and/or age-regressed and/or Z transformed or F ratio transformed or otherwise statistically assessed, based upon the normative reference database.

16. A method as in claim 10 wherein the subject's digital data is derived from 19 magnetic field detectors and quantitative features derived therefrom are compared to similar features from data derived from 19 EEG electrodes corresponding in location to the full 10/20 system.

17. A method as in claim 10 wherein the detecting of the analog magnetic fields is accomplished by positioning a helmet-shaped dewar tail over the scalp of the subject, aligning the subject's head with fiducial marks on the dewar tail, and holding the subject's head firmly in the dewar tail to prevent head movement.

18. The method of analyzing the brain waves of a human subject to determine the presence, absence, degree and type of magnetic evoked response abnormality, the method consisting of the steps, in sequence, of:
    (a) positioning a plurality of magnetic field detectors in an array proximate to the scalp of the subject, the detectors being positioned in the same relative positions over the scalp as at least some of the electrodes are positioned in the 10/20 system; automatically presenting a sequence of stimuli to the subject to evoke magnetic brain responses (MER) at the detectors;

(b) detecting, amplifying, converting the amplified electromagnetic brain activity from each detector into digital data, averaging the digitized brain activity to provide a set of averaged magnetic evoked responses (AMERs) from the array;

(c) decomposing each of the averaged magnetic evoked responses (AMER) by factor analysis, in which each AMER from each detector is compared to pre-formulated factor waveforms (or component shapes) stored in computer memory to determine the amount of power that each pre-formulated factor waveform contributes to said AMER to thereby produce a factor score $a_{ij}$, quantifying the contribution of each factor j to the AMER from any detector i;

(d) subjecting the results of the said factor score to Z transform, wherein each of said factor scores is compared to the statistical parameters of a normative factor score, corresponding to a quantitative assessment of AMER morphology, thereby providing an estimate of the degree of abnormality of each of said AMER'S.

19. The method of claim 18 and displaying the said normality and degree of abnormality on a color-coded sectored or interpolated topographic map comprising a head diagram in which each area of the head represents a detector location and the colors represent normality and the degree of abnormality reflected by each factor Z score.

20. The method of claim 19 wherein a series of topographic maps correspond to the anatomical distribution of Z-scores for each factor, a map indicating the % of local AMER variance which cannot thereby be accounted for (residual), and a map depicting the square root of the sum of Z-scores at each detector $$\left| \sum_{i=i}^{M} z_i^2 \right|^{1/2}$$

or total abnormal morphology.

21. The method of claim 18 and positioning 19 detectors in the same relative positions as the 19 active electrodes in the 10/20 EEG system.

22. The method of claim 18 wherein the stimuli presented are a series of flashes or other visual stimuli to produce visual magnetic evoked responses (VMERs).

23. The method of claim 18 wherein the stimuli presented are a series of clicks or other auditory stimuli to produce auditory magnetic evoked responses (AMERs).

24. The method of claim 18 wherein the stimuli presented are a series of electrical shocks or other somatosensory stimuli to produce somatosensory magnetic evoked responses (SMER's).

25. A system for detecting and analyzing the magnetic fields on the scalp of the subject arising from the subject's brain activity, comprising:

(a) means for detecting and amplifying analog magnetic fields including a plurality of magnetic field detectors adapted to be positioned adjacent selected areas of the subject's scalp to produce amplified signals in a plurality of channels;

(b) means for converting the amplified signals into digital data;

(c) computer means for automatically comparing quantitative features extracted from the digital data with statistical parameters of a feature database based on EEG (Quantitative Electroencephalogram) of normal subjects, the comparison being on the basis of the same features obtained at the same location of field detectors for the subject as EEG electrodes that had been positioned on the normal subjects to generate the database.

26. A system as in claim 25 wherein the means for detecting the analog magnetic fields includes a helmet-shaped dewar tail adapted to be positioned over the scalp of the subject, means for aligning the subject's head relative to the dewar tail including fiducial marks on the dewar tail, and means or holding the subject's head firmly in the dewar tail to prevent head movement.

27. A system as in claim 25 wherein the areas selected on the subject's scalp correspond in location to areas to which at least some of the EEG electrodes of the 10/20 system are normally connected.

28. A system as in claim 25 and a SQUID as part of each magnetic field detector.

29. A system as in claim 25 and a magnetometer or gradiometer as part of each magnetic field detector.

30. A system as in claim 25 and means to Z transform or F ratio transform features extracted from the digital data derived from each magnetic field detector based upon the normative reference database.

31. A system as in claim 25 wherein the subject's digital data is derived from 19 magnetic field detectors and is compared to data derived from 19 EEG electrodes corresponding in location to the full 10/20 system.

32. A system for detecting and analyzing the magnetic fields on the scalp of a subject arising from the subject's brain activity, comprising:

(a) a plurality of magnetic field detectors arranged in an array in a dewar tail adapted to be positioned on the subject's scalp, with the array corresponding in location to at least some of the EEG electrode locations in the 10/20 EEG system;

(b) means for amplifying and digitizing analog signals from the magnetic field detectors to produce a set of digital data corresponding to the analog signals from each magnetic field detector;

(c) computer means for automatically comparing quantitative features extracted from each set of digital MEG data taken under selected conditions or stimuli with features of Quantitative Electroencephalogram (QEEG) digital data collected from a normal group under the same conditions or stimuli and at the same scalp locations as the locations of the magnetic field detectors on the subject's scalp.

33. A system as in claim 32 wherein the array comprises 19 magnetic field detectors arranged in locations corresponding to the locations of the 19 active electrodes of the 10/20 EEG system.

34. A system as in claim 32 wherein each magnetic field detector comprises a magnetometer or gradiometer and a SQUID and the dewar tail has a helmet-shaped cavity adapted to be brought into close proximity to the scalp of the subject.

35. A magnetoencephalogram (MEG) system for detecting and analyzing magnetic fields on the scalp of a subject generated by the subject's brain activity, comprising:

(a) an array of a plurality of magnetic field detectors adapted to be positioned closely adjacent the subject's scalp to detect and amplify magnetic fields from selected areas of the scalp;

(b) means for converting the detected magnetic fields into sets of digital data, with each set being generated by a magnetic field detector;

(c) computer means for automatically comparing quantitative features extracted from the sets of digital data with a normative reference database of such features simultaneously or previously collected from normal subjects, the comparisons being on a feature-by-feature basis, and the normal subjects having generated the database using EEG electrodes at the same relative locations on their scalps as the relative locations of the magnetic field detectors on the scalp of the subject;

(d) computer means for deriving a discriminant score based on the comparisons of (c) by selecting, weighting, and combining a number of said feature-by-feature comparisons;

(e) computer means for combining the discriminant scores to derive probabilities that the subject is classified in a specific diagnostic category;

(f) computer means for applying selected guardbands (rule-out levels) to the probabilities to classify the subject on the basis of the probabilities; and (g) means for displaying the classification of the subject.

36. The system of claim 35 in which the normative reference database of features is used to generate age-corrected Z-scores which are in the same dimensional unit.

37. A magnetoencephalogram (MEG) system for analyzing the magnetic components of a human subject's brain activity which are evoked by stimuli to determine the abnormality or normality of the response morphology, the system consisting of:

(a) a plurality of MEG magnetic-field detectors, i, a dewar tail containing the field detectors, means to bring the dewar tail proximate the scalp of the subject to detect the subject's brain activity, the detectors being positioned in the same relative positions over the scalp as at least some of the electrodes are positioned in the 10/20 system; stimuli means for automatically presenting a sequence of stimuli to the patient to evoke brain magnetic responses (MER) at the field detectors;

(b) amplifier means for amplifying the MER's, A/D converter means for converting the amplified AMERs into digital data, averaging means for averaging the digital data to provide averaged magnetic evoked responses (AMERs) for analysis;

(c) computer means having a computer memory and calculation means for analyzing the AMERs by factor analysis, said computer means comparing each AMER from each field detector i to pre-formulated factor wave forms, j, stored in the computer memory to determine the power that each pre-formulated factor waveform, j, contributes to the AMER from detector i producing a factor score $a_{ij}$ quantifying the contribution of each factor to the AMER from any field detector i;

(d) computer means for subjecting said factor score, $a_{ij}$, to Z-transform, $Z_{ij}$, or F-value, $F_{ij}$, automatically comparing each of said factor scores to the statistical parameters of a normative factor score database stored in the computer memory to produce a statistical assessment enabling a determination of response normality versus the degree of abnormality of morphology, and (e) display means to display the said normality and degree of abnormality.

38. A system as in claim 37 wherein the display of (e) is a color coded topographic map comprising a head diagram in which each area of the head represents a magnetic detector location and the color represents a statistical estimate of the degree of abnormality reflected by the factor Z-score or F-value.

39. The system of claim 37 wherein the stimuli presented are a series of flashes or other visual stimuli to produce visual magnetic evoked responses (VMERs).

40. The system of claim 37 wherein the stimuli presented are a series of clicks or other auditory stimuli to produce auditory magnetic evoked potentials (AMERs).

41. The system of claim 37 wherein the stimuli presented are a series of electrical shocks or other somatosensory stimuli to produce somatosensory magnetic evoked responses (SMERs).

42. The system of claim 37 wherein a set of topographic maps depict the spatial (anatomical) distribution of each factor Z-score, the overall abnormality of the response morphology at each derivation $$\sum_{i=i}^{M} |Z_i^2|^{1/2}$$

and the residual variance unaccountable by the normal factors.

* * * * *